US011957350B2

(12) United States Patent
Basu et al.

(10) Patent No.: US 11,957,350 B2
(45) Date of Patent: Apr. 16, 2024

(54) LIGATION BAND DEVICE AND METHOD FOR DEPLOYING LIGATION BANDS

(71) Applicant: BOSTON SCIENTIFIC LIMITED, Hamilton (BM)

(72) Inventors: Abhishek Basu, Gurgaon (IN); Rohit Rohilla, Rohtak (IN); Hitendra Purohit, Vadodara (IN); Agrim Mishra, New Dehli (IN); Nabarun Bhowmick, Kolkata (IN); Nidhi Dhingra, Ludhiana (IN); Balaji Aswatha Narayana, Bangalore (IN); Deepak Kumar Sharma, Muzaffarnafar (IN)

(73) Assignee: BACON SCIENTIFIC LIMITED, Hamilton (BM)

( * ) Notice: Subject to any disclaimer, the term of this patent is extended or adjusted under 35 U.S.C. 154(b) by 810 days.

(21) Appl. No.: 16/922,695

(22) Filed: Jul. 7, 2020

(65) Prior Publication Data
US 2021/0007749 A1 Jan. 14, 2021

Related U.S. Application Data

(60) Provisional application No. 62/871,327, filed on Jul. 8, 2019.

(51) Int. Cl.
*A61B 17/12* (2006.01)

(52) U.S. Cl.
CPC ............ *A61B 17/12013* (2013.01); *A61B 2017/12018* (2013.01)

(58) Field of Classification Search
CPC .............. A61B 17/12; A61B 17/12013; A61B 17/12009; A61B 2017/12004; A61B 2017/12018
See application file for complete search history.

(56) References Cited

U.S. PATENT DOCUMENTS 5,681,328 A 10/1997 Lamport et al.
5,980,537 A 11/1999 Ouchi
(Continued)

FOREIGN PATENT DOCUMENTS

CN 102639068 8/2012
CN 109069159 12/2018
(Continued)

OTHER PUBLICATIONS

Cheng-hua et al., "Development of a new type of hemorrhoids ligation device", China Medical Equipment, DOI: 10.3969/J.ISSN. 1672-8270, Jun. 15, 2013, 2 sheets.

*Primary Examiner* — Timothy J Neal
*Assistant Examiner* — Mohammed S Adam
(74) *Attorney, Agent, or Firm* — Fay Kaplun & Marcin, LLP (57) ABSTRACT

A device includes an elongated hollow member having an open distal end for receiving tissue therein and at least one exterior groove for loading at least one ligation band thereon. The device also includes a band deployment sleeve slidable over the exterior of the hollow member and configured to move from a radially expanded position to a radially contracted position in which, when the band deployment sleeve slides longitudinally over the hollow member, the distal portion engages the at least one ligation band. A closing sleeve slidable over the exterior of the band deployment sleeve is configured to constrain the distal portion from the radially expanded position into the radially contracted position. Retracting the closing sleeve proximally over the distal portion of the band deployment sleeve releases the distal portion from the radially contracted position into the radially expanded position.

10 Claims, 11 Drawing Sheets

(56) References Cited

U.S. PATENT DOCUMENTS

| | | |
|---|---|---|
| 6,436,108 B1 | 8/2002 | Mears |
| 2002/0072757 A1 | 6/2002 | Ahmed et al. |
| 2010/0063517 A1 | 3/2010 | Cleator |
| 2011/0077666 A1 | 3/2011 | McCahon et al. |
| 2014/0364873 A1 | 12/2014 | Smith et al. |
| 2018/0092644 A1 | 4/2018 | Wallis |
| 2018/0235636 A1 | 8/2018 | Culbert et al. |

FOREIGN PATENT DOCUMENTS

| | | |
|---|---|---|
| EP | 0 679 368 | 11/1995 |
| EP | 2 272 445 | 1/2011 |
| WO | 96/19145 | 6/1996 |
| WO | 2005/039421 | 5/2005 |
| WO | 2015/006083 | 1/2015 |

LIGATION BAND DEVICE AND METHOD FOR DEPLOYING LIGATION BANDS

PRIORITY CLAIM

The present disclosure claims priority to U.S. Provisional Patent Application Ser. No. 62/871,327 filed Jul. 8, 2019; the disclosure of which is incorporated herewith by reference.

FIELD

The present disclosure relates to the treatment of hemorrhoids and, in particular, relates to a device for ligating hemorrhoids using multiple ligation bands and holding members to draw in hemorrhoid tissue.

BACKGROUND

Hemorrhoids are swollen and inflamed veins around the anus or in the lower rectum. Hemorrhoids may be external, forming under the skin around the anus, or internal, forming in the lining of the anus and the lower rectum.

Rubber band ligation (RBL) is a method for treating hemorrhoids. A rubber band is placed at the base of the hemorrhoid strangulating blood flow thereto, so that the reducing inflammation and eventually eliminating the hemorrhoid. The hemorrhoid is hemorrhoid eventually falls off and is passed out of the body. Many RBL systems incur high cost and/or suffer from high failure rates or recurrence rates due to the difficulty of applying a ligation band directly to the root of the hemorrhoid.

SUMMARY

The present disclosure relates to a device comprising an elongated hollow member having an open distal end for receiving tissue therein and at least one exterior groove for loading at least one ligation band thereon. The device further comprises a band deployment sleeve slidable over the exterior of the hollow member, the band deployment sleeve having a distal portion configured to move from a radially expanded position in which, when the band deployment sleeve slides longitudinally over the hollow member, the distal portion is disengaged from the at least one ligation band, to a radially contracted position in which, when the band deployment sleeve slides longitudinally over the hollow member, the distal portion engages the at least one ligation band. The device further comprises a closing sleeve slidable over the exterior of the band deployment sleeve so that moving the closing sleeve distally over the distal portion of the band deployment sleeve constrains the distal portion from the radially expanded position into the radially contracted position and retracting the closing sleeve proximally over the distal portion of the band deployment sleeve releases the distal portion from the radially contracted position into the radially expanded position.

An embodiment further comprises, a pin on the interior of the closing sleeve slidable within a slot in the band deployment sleeve, wherein moving the closing sleeve distally over the distal portion of the band deployment sleeve causes the pin to slide distally within the slot until the pin abuts a distal end of the slot and further distal movement of the closing sleeve engages the pin with the distal end of the slot and moves the band deployment sleeve distally.

In an embodiment, when the at least one ligation band is loaded in the groove, the distal movement of the band deployment sleeve pushes the ligation band out of the groove and off the distal end of the hollow member.

In an embodiment, the elongated hollow member has a plurality of exterior grooves arranged in a longitudinal series on the elongated hollow member for loading a plurality of ligation bands thereon, wherein, when each of the plurality of ligation bands are loaded in the plurality of grooves, the distal movement of the band deployment sleeve in the radially contracted position pushes a furthest distal ligation band out of a furthest distal groove and off the distal end of the hollow member and shifts additional ligation bands distally by one groove of the longitudinal series.

In an embodiment, the distal portion of the band deployment sleeve comprises a plurality of flexible members, each flexible member having a plurality of teeth arranged in a longitudinal series on the flexible member so that the distal movement of the band deployment sleeve in the radially contracted position causes each tooth to engage one of the plurality of ligation bands.

In an embodiment, after the further distal movement of the closing sleeve, moving the closing sleeve proximally over the distal portion of the band deployment sleeve causes the pin to slide proximally within the slot until the pin abuts a proximal end of the slot and further proximal movement of the closing sleeve engages the pin with the proximal end of the slot and moves the band deployment sleeve proximally.

In an embodiment, the proximal movement of the closing sleeve causes the band deployment sleeve to open into the radially expanded position and the further proximal movement of the closing sleeve returns the band deployment sleeve to an initial position without causing the teeth to engage the additional ligation bands.

In an embodiment, at least one of the plurality of ligation bands is color-coded for notifying an operating medical professional of a additional number of ligation bands.

An embodiment further comprises, a vacuum port extending transverse to the hollow member for attaching a suction hose and inducing suction at the open distal end of the hollow member.

An embodiment further comprises, a spool coupled to a proximal end of the closing sleeve and slidable over the elongated hollow member; and a thumb ring coupled to a proximal end of the elongated hollow member, wherein separating the thumb ring and the spool causes the closing sleeve to move distally.

The present disclosure also relates to a method comprising receiving tissue through an open distal end of an elongated hollow member of a device, the hollow member having at least one exterior groove for loading at least one ligation band thereon. The method further comprises moving a closing sleeve distally over the exterior of a band deployment sleeve, the distal sliding of the closing sleeve forcing a distal portion of the band deployment sleeve from a radially expanded position in which, when the band deployment sleeve slides longitudinally over the hollow member, the distal portion is disengaged from the at least one ligation band to a radially contracted position in which, when the band deployment sleeve slides longitudinally over the hollow member, the distal portion engages the at least one ligation band.

An embodiment further comprises, moving the closing sleeve further distally so that a pin on the interior of the closing sleeve engages a distal end of a slot in the band deployment sleeve so that the further distal movement of the closing sleeve moves the band deployment sleeve distally.

In an embodiment, when the at least one ligation band is loaded in the groove, the distal movement of the band deployment sleeve pushes the ligation band out of the groove and off the distal end of the hollow member.

In an embodiment, the elongated hollow member has a plurality of exterior grooves arranged in a longitudinal series on the elongated hollow member for loading a plurality of ligation bands thereon, wherein, when each of the plurality of ligation bands are loaded in the plurality of grooves, the distal movement of the band deployment sleeve in the radially contracted position pushes a furthest distal ligation band out of a furthest distal groove and off the distal end of the hollow member and shifts additional ligation bands distally by one groove of the longitudinal series.

In an embodiment, the distal portion of the band deployment sleeve comprises a plurality of flexible members, each flexible member having a plurality of teeth arranged in a longitudinal series on the flexible member so that the distal movement of the band deployment sleeve in the radially contracted position causes each tooth to engage one of the plurality of ligation bands.

An embodiment further comprises, retracting the closing sleeve proximally over the distal portion of the band deployment sleeve, the proximal retraction of the closing sleeve causing the pin to slide proximally within the slot until the pin abuts a proximal end of the slot and further proximal movement of the closing sleeve engages the pin with the proximal end of the slot and moves the band deployment sleeve proximally.

In an embodiment, the proximal movement of the closing sleeve causes the band deployment sleeve to open into the radially expanded position and the further proximal movement of the closing sleeve returns the band deployment sleeve to an initial position without causing the teeth to engage the additional ligation bands.

In an embodiment, at least one of the plurality of ligation bands is color-coded for notifying an operating medical professional of an additional number of ligation bands.

An embodiment further comprises, inducing suction at the open distal end of the hollow member with a suction hose attached to the hollow member via a vacuum port transverse to the hollow member.

In an embodiment, the closing sleeve is moved distally by separating a thumb ring coupled to a proximal end of the elongated hollow member and a spool coupled to a proximal end of the closing sleeve, the spool being slidable over the elongated hollow member.

BRIEF DESCRIPTION

DETAILED DESCRIPTION

The present disclosure may be further understood with reference to the following description and the appended drawings, wherein like elements are referred to with the same reference numerals. The present disclosure may be directed to a single-use rubber band ligation device with plunger actuation and camera visualization. The exemplary device may advance through a series of configurations to deploy a first ligation band and return to its original configuration to subsequently deploy further ligation bands. It is further noted that the terms proximal and distal, as used herein, refer to a direction toward (proximal) and away from (distal) a user of the device.

Figure 1:
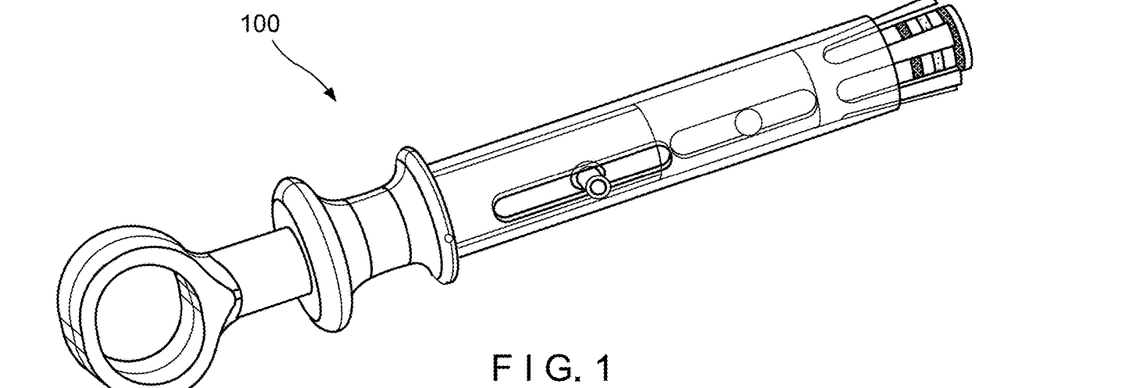
FIG. 1 shows a perspective view of a device for ligating hemorrhoids according to a first exemplary embodiment of the present disclosure.
Figure 2:
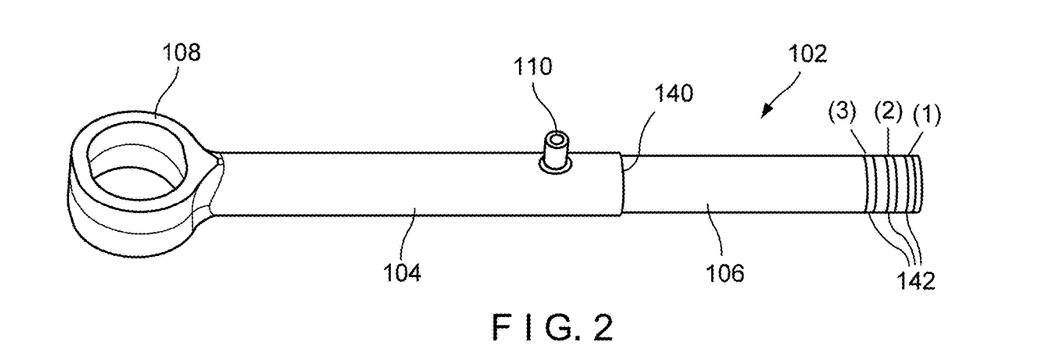
FIG. 2 shows a perspective view of a plunger of the device of FIG. 1.

As shown in FIGS. 1-10, a device 100 for ligating hemorrhoids includes a plunger 102 that, in an exemplary embodiment, spans the full longitudinal length of the device 100. The plunger 102 may have an elongate body, e.g., a hollow tube. The plunger 102 comprises a proximal portion 104, a distal portion 106 and a thumb ring 108, as shown in FIG. 2. The proximal portion 104 has an outer diameter slightly greater than the diameter of the distal portion 106, forming a step 140 at the intersection of the two portions 104, 106 of the plunger 102. The plunger 102 of this embodiment may be substantially tubular, having an interior sized to receive a hemorrhoid during a ligation procedure. The thumb ring 108 is disposed at a proximal end of the proximal portion 104 and is sized for receiving an operating medical professional's thumb during the procedure.

In one embodiment, a distal end of the distal portion 106 may have a plurality of circumferential slots 142 for loading ligation bands 150 thereon for deployment onto one or more hemorrhoids during the procedure. The slots 142 may have various structures that are described in greater detail below. In embodiments, the device 100 may have any number of slots 142 for loading an equivalent number of ligation bands 150, for performing a hemorrhoid treatment procedure. In some embodiments, the device 100 may have between two and seven slots for loading between two and seven ligation bands 150, and in embodiments, the device 100 may have three slots 142 for loading up to three ligation bands 150. Although the device 100 will be described as having three slots 142 for three ligation bands 150, it will be understood that in alternate embodiments the device 100 may have more or less slots and/or ligation bands loaded thereon. A circumferential slot 142(1) is the most distal slot, slot 142(2) is the middle slot, and slot 142(3) is the most proximal slot, and the slots 142(1)-142(3) may be circumferential grooves, or tapered flanges, in the distal portion 106 of the device 100 for each receiving and retaining ligation bands 150.

The ligation bands 150 may be formed of an elastomeric material and may be extended to a stretched position to fit over the distal portion 106. The bands may be received and retained on the distal portion 106 and held in position by their elasticity until deployment as desired by a medical professional. A vacuum port 110 on the proximal portion 104 of the plunger 102 is a fitting extending transverse to the proximal portion 104 and to provide access to the hollow interior of the plunger 102. During the procedure, a suction hose (not pictured) may be connected to the vacuum port 110 to provide negative pressure and draw the target tissue (e.g., the hemorrhoid) into the distal portion 106 of the device 100. After the hemorrhoid has been drawn into the device 100 a band deployment mechanism 114 is actuated to push a first ligation band 150 in the distal slot 142(1) distally off the distal end of the device 100 so that it constricts about the base of the hemorrhoid that has been drawn into the device 100.

A spool 112 is slidably coupled to the exterior of the proximal portion 104, having an aperture with an inner diameter corresponding to the outer diameter of the proximal portion 104. The spool 112 has a concave shape between a proximal end and a distal end. A medical professional grips the device 100 inserting a thumb into the thumb ring 108 and, for example, middle and index fingers on the concave portion of the spool 112, to apply a force to separate the ring 108 and the spool 112 and advance the spool 112 distally along the proximal portion 104 of the plunger 102 to actuate the band deployment mechanism 114, as will be described in greater detail below with respect to FIG. 8.

Figure 4:
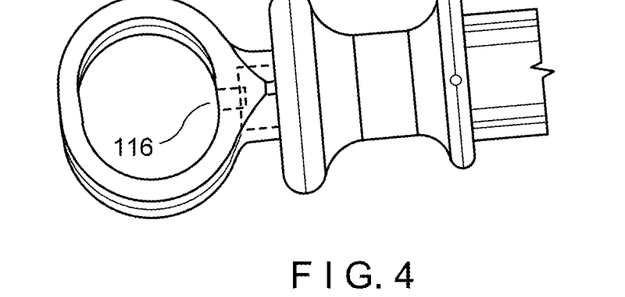
FIG. 4 shows a side view of a proximal end of the device of FIG. 1.

A camera 116 is disposed on a distal end of the thumb ring 108, as shown in FIG. 4, and has a lens pointing distally down the interior of the hollow plunger 102 and out the distal end of the distal portion 106, permitting visualization of the procedure, for example, on a screen (not pictured). The camera 116 may be either wired or wireless. If wired, an endoscopic cable may be attached to the camera 116, for example, through a suitable opening provided on the thumb ring. In embodiments, the camera 116 may be removably attachable to the device 100, such that the device 100 may be a single use device, and the camera 116 may be reusable in multiple devices 100.

Figure 5:
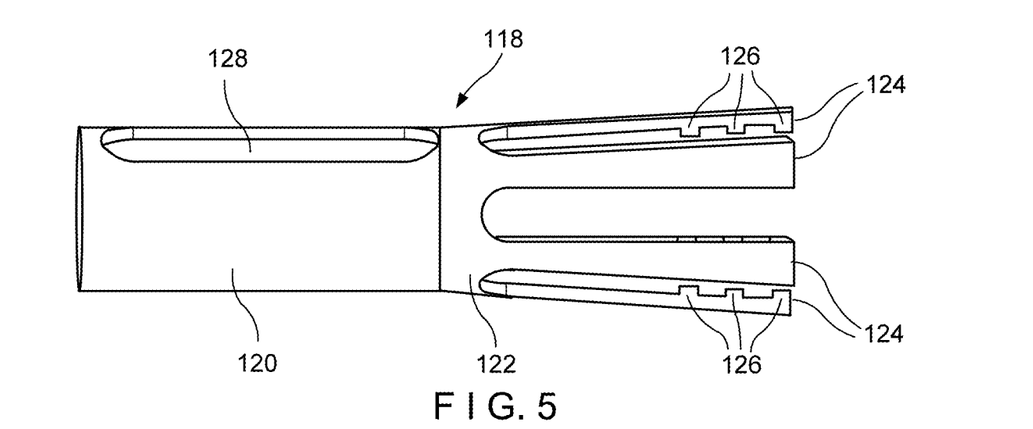
FIG. 5 shows a side view of a band deployment sleeve of the device of FIG. 1.
Figure 8:
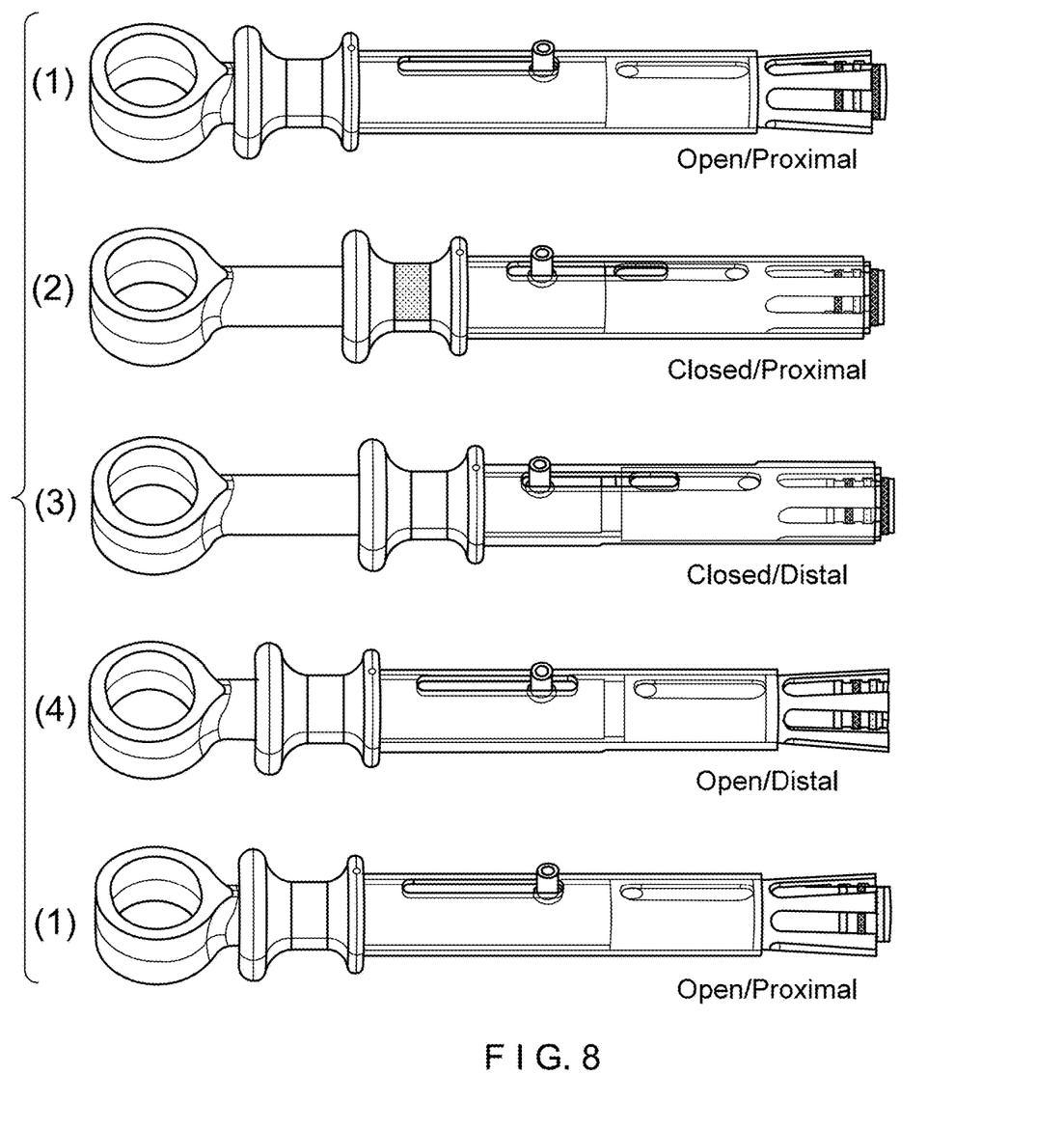
FIG. 8 shows the device of FIG. 1 advancing through a series of configurations during a ligation procedure.

The band deployment mechanism 114 includes a band deployment sleeve 118, as shown in FIG. 5, slidably coupled to the exterior of the distal portion 106 of the plunger 102. The band deployment sleeve 118 may be a substantially elongate body, e.g., hollow tube, and disposed coaxially with the plunger 102. A proximal portion 120 of the band deployment sleeve 118 is in slidable contact with the distal portion 106 of the plunger 102. A proximal end of the proximal portion 120 abuts the step 140 between the proximal portion 104 and the distal portion 106 when the device 100 is in a first (unactuated) and second configurations, as shown in FIG. 8. A distal portion of the band deployment sleeve 118 is a flexible band pushing portion 122 adjustable between a radially expanded position and a radially contracted position. The radially expanded position may be referred to as an "open position" and the radially contracted position may be referred to as a "closed position" herein. In the open position the pushing portion 122 has a radius that gradually increases from a minimum at the proximal end to an increased diameter as the sleeve 118 terminates at a distal end.

The pushing portion 122 of this embodiment comprises a plurality of flexible flanges 124 fanning out and partially circumscribing a conical frustum space when the pushing portion 122 is in the open position. In embodiments, any number of flanges 124 may be equidistantly circumferentially disposed around the pushing portion 122. In some embodiments, six flexible flanges 124 may be equidistantly disposed circumferentially around the pushing portion 122. The pushing portion 122 is in the open position when the device 100 is in a first and fourth configuration. The pushing portion 122 is bendable from the open position to the closed position. In some embodiments, the flanges 124 may be biased in an open position and may have a spring force such that in an unconstrained configuration, the flanges 124 are in the open position.

In the closed position the pushing portion 122 is constrained into a substantially cylindrical shape. Each of the flexible flanges 124 may have a plurality of teeth 126 protruding radially inward and disposed spaced apart from each other along the flange 124, from a proximal end to a distal end of the flange 124. In embodiments, the flanges 124 may have any number of teeth 126, and in some embodiments may have an equal number of spaces between teeth for receiving ligation bands 150. For example, each flange 124 may have between two and seven teeth, and in some embodiments, each flange 124 may have three teeth. It is understood that teeth 126 on each flange 124 may be in alignment with teeth 126 on corresponding flanges 124, so that ligation bands 150 may be disposed in the resulting circumferential space between the teeth 126.

In the closed position the teeth 126 are brought into a position contacting, or close to contacting, the exterior of the distal portion 106 of the plunger 102. The deployment sleeve 118 and the plunger 102 are arranged such that in the second configuration of the device 100 each of the teeth 126 is brought into a position immediately proximal to each of the circumferential slots 142 and the pre-loaded ligation bands 150. In other words, in the second configuration a first tooth 126 of each flange 124 is positioned immediately proximal to the slot 142(1), a second tooth 126 is positioned immediately proximal to the slot 142(2), and a third tooth 126 is positioned immediately proximal to the slot 142(3). In this manner, as the band deployment mechanism 114 is slid distally over the plunger 102 from the second configuration to a third configuration, each of the teeth 126 engages and pushes a corresponding one of the ligation bands 150 forward, as will be described in more detail below.

The teeth 126 may contact the exterior of the distal portion 106, or the pushing portion 122 may be brought into a sufficiently contracted state such that the teeth 126 will engage the ligation bands 150 when the band deployment mechanism 114 is slid distally, but the teeth 126 do not directly contact the exterior of the distal portion 106. The proximal end 120 of the deployment sleeve 118 includes at least one longitudinal slot 128 in which a pin 134 of a closing sleeve 130 travels. The proximal end 120 of the deployment sleeve 118 may include a single longitudinal slot 128 or a plurality of slots 128. When the deployment sleeve has more than one slot 128 the closing sleeve 130 of this embodiment will have a corresponding pin 134 for each of the slots 128. For example, FIG. 7 shows an embodiment where the closing sleeve 130 has two pins 134 corresponding to two slots 128.

Figure 3:
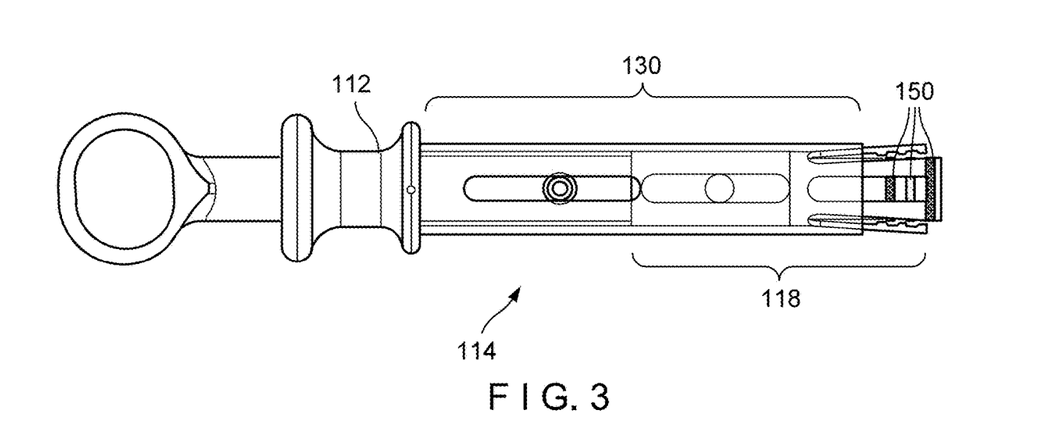
FIG. 3 shows a side view of the device of FIG. 1.
Figure 6:
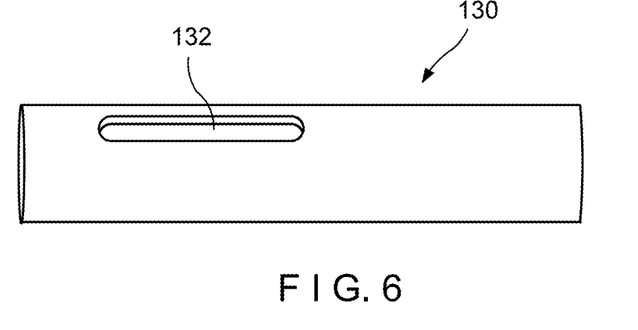
FIG. 6 shows a side view of a closing sleeve of the device of FIG. 1.
Figure 7:
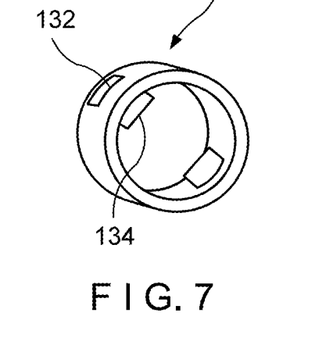
FIG. 7 shows a perspective view of the closing sleeve of the device of FIG. 1.

The closing sleeve 130, as shown in FIGS. 6-7, is a second component of the band deployment mechanism 114 of this embodiment and is configured to operate the deployment sleeve 118 between the open position and the closed position. The closing sleeve 130 is a hollow member disposed longitudinally about the exterior of the plunger 102 and the deployment sleeve 118, as shown in FIG. 3. The closing sleeve is in slidable contact with the exterior of the deployment sleeve 118. In the first configuration of the device 100, the closing sleeve 130 extends longitudinally from the distal end of the spool 112 to the proximal end of the flexible band pushing portion 122 of the band deployment sleeve 118. The closing sleeve 130 and the spool 112 are coupled together by, e.g., an adhesive, bonding, welding, brazing, soldering, or mechanical fastener, or combinations thereof.

Alternately, the components may be fashioned as a half spool and a half closing sleeve piece bonded with a corresponding half spool/half closing sleeve piece. In either embodiment, the closing sleeve 130 and the spool 112 move together as one piece once assembled. In a proximal position, the closing sleeve 130 may not yet contact the pushing portion 122 of the deployment sleeve 118, such that the pushing portion 122 is in the open position in the first configuration of the device 100. When the spool 112 is advanced distally, the interior diameter of the closing sleeve 130 constrains the flanges 124 of the pushing portion 122 of the deployment sleeve 118 into the closed position, engaging the teeth 126 with the exterior of the plunger 102 proximal to the bands 150. The closing sleeve 130 includes a longitudinal slot 132 sized to accommodate the vacuum port 110 and the suction hose during the ligation procedure. The slot 132 allows the closing sleeve 130 to slide over the plunger 102 without interfering with the vacuum port 110, as seen in FIG. 8.

The pin 134 is disposed on the interior of the closing sleeve 130 distal to the slot 132. The pin 134 is configured to travel within the slot 128 of the deployment sleeve 118 to maintain alignment. When the spool 112 is pushed distally the pin 134 advances distally in the deployment sleeve slot 128, engaging the distal end of the deployment sleeve slot 128 and pushing the deployment sleeve 118 and a ligation band 150 off the distal end of the plunger 102.

Conversely, when the spool 112 is drawn proximally, the pin 134 travels the length of the deployment sleeve slot 128 and engages the proximal end of the slot 128 to pull the deployment sleeve 118 back to a proximal position. Thus, it may be seen that deployment sleeve 118 is movable only a small distance, i.e., from a first position proximal to the bands 150 to a second position in which all the bands 150 have been pushed forward by one position. A first band 150 originally in the first band position, i.e. the slot 142(1), is pushed onto the hemorrhoid, while a second band 150 originally in the second band position, i.e. the slot 142(2) is pushed to the first band position and a third band 150 originally in the third band position, i.e. the slot 142(3) is pushed to the second band position.

The operation of the device 100 will be described in relation to the four configurations shown in FIG. 8. The configurations may be considered with respect to the positioning of the deployment sleeve 118. As described previously, the deployment sleeve 118 may be either open or closed and either proximal or distal. For example, the four configurations of the deployment sleeve are open/proximal, closed/proximal, closed/distal and open/distal, as will be described below.

The first configuration of the device 100 is the unactuated starting position. In the first configuration the spool 112 is retracted fully proximally, abutting the thumb ring 108. The closing sleeve 130, which may be attached to the spool 112, is accordingly at its most distal position, in which the vacuum port 110 abuts the distal end of the closing sleeve slot 132 and the pin 134 abuts the proximal end of the deployment sleeve slot 124. The deployment sleeve 118 is in the open/proximal position, with the distal end of the closing sleeve 130 disposed at the proximal end of the pushing portion 122 of the deployment sleeve 118. Because the deployment sleeve 118 is in the open position the pushing portion 122 is fanned and the teeth 126 are not in contact with the exterior of the plunger 102.

The spool 112 has a two-part forward stroke that advances the device 100 into second and third configurations. For the first part of the stroke, and advancement into the second configuration, the spool 112 is advanced distally along the plunger 102, positioning the closing sleeve 130 onto the pushing portion 122 of the deployment sleeve 118 and into the closed position (e.g., constraining the flanges 124). The first part of the stroke brings the pin 134 of the closing sleeve 130 to a position abutting the distal end of the deployment sleeve slot 128. It is understood that the deployment sleeve 118 is still in the proximal position, i.e. proximal/closed, in the second configuration. In other words, the spool 112 advances far enough distally to close the pushing portion 120 but not so far distally as to engage the pin 134 against the distal portion of the deployment sleeve slot 128.

The second part of the forward stroke of the spool 112 advances the device 100 into the third configuration whereby the pin 134 pushes the deployment sleeve 118 distally (to the distal/closed position), engaging the teeth 126 with the bands 150 and pushing each band forward by one band position. The first band is deployed over tissue received in the device 100, and the remaining/additional bands assume the first and second band positions. The deployment sleeve 118 and the spool 112 may move in tandem over the plunger 112 during the second part of the forward stroke, such that the deployment sleeve 118 no longer abuts the step 140 on the plunger 112 in the third configuration.

Advancement to the third configuration deploys a band 150 at the base of a hemorrhoid. The spool 112 has a two-part return stroke for advancing the device 100 into the fourth configuration and ultimately back to the first configuration. As the spool 112 retracts the closing sleeve 130 moves proximally, enabling the release of the pushing portion 122 into the open (fanned) position. The pin 134 on the closing sleeve 130 moves proximally through the deployment sleeve slot 124. It is noted that the deployment sleeve 118 remains in the distal position as it moves to the open position of the fourth configuration. The fourth configuration is reached when the spool 112 has traveled far enough proximally for the distal end of the closing sleeve 130 to reach the proximal end of the pushing portion 122 and for the pin 134 to abut the proximal end of the deployment sleeve slot 128. The deployment sleeve 118 is now in the open/distal position.

The second part of the return stroke returns the device 100 to the first configuration. The spool 112 pulls the pin 134 against the proximal end of the deployment sleeve slot 128

As before, the spool/closing sleeve are locked with the deployment sleeve 118 via the pin 134, so the spool 112 sliding proximally over the plunger 102 is akin to sliding the deployment sleeve 118 proximally over the plunger 102. The open position of the pushing portion 122 allows the teeth 126 to clear the remaining two ligation bands 150 as the teeth 126 are drawn proximally and repositioned for deployment of the remaining two bands 150. It may be seen that the deployment sleeve slot 128 is longitudinally sized specifically to accommodate the distance the closing sleeve 130 travels to close the pushing portion 122, yet short enough to engage the pin 134 on both the distally directed (forward) stroke and the proximally directed (backward) stroke.

After the application of the first band 150 to the hemorrhoid a medical professional may apply the remaining two bands 150 to any remaining hemorrhoids in a manner substantially similar to the process described above. A second band deployment will push the third band to the first band position, and a third band deployment will exhaust the ligation bands 150 of the device having three ligation bands 150. The device 100 may be used in a similar manner to deploy any number of pre-loaded ligation bands 150. Thus, it may be seen that the device 100 may be a single-use disposable ligation device or may be reloaded for the application of additional ligation bands 150.

Figure 9:
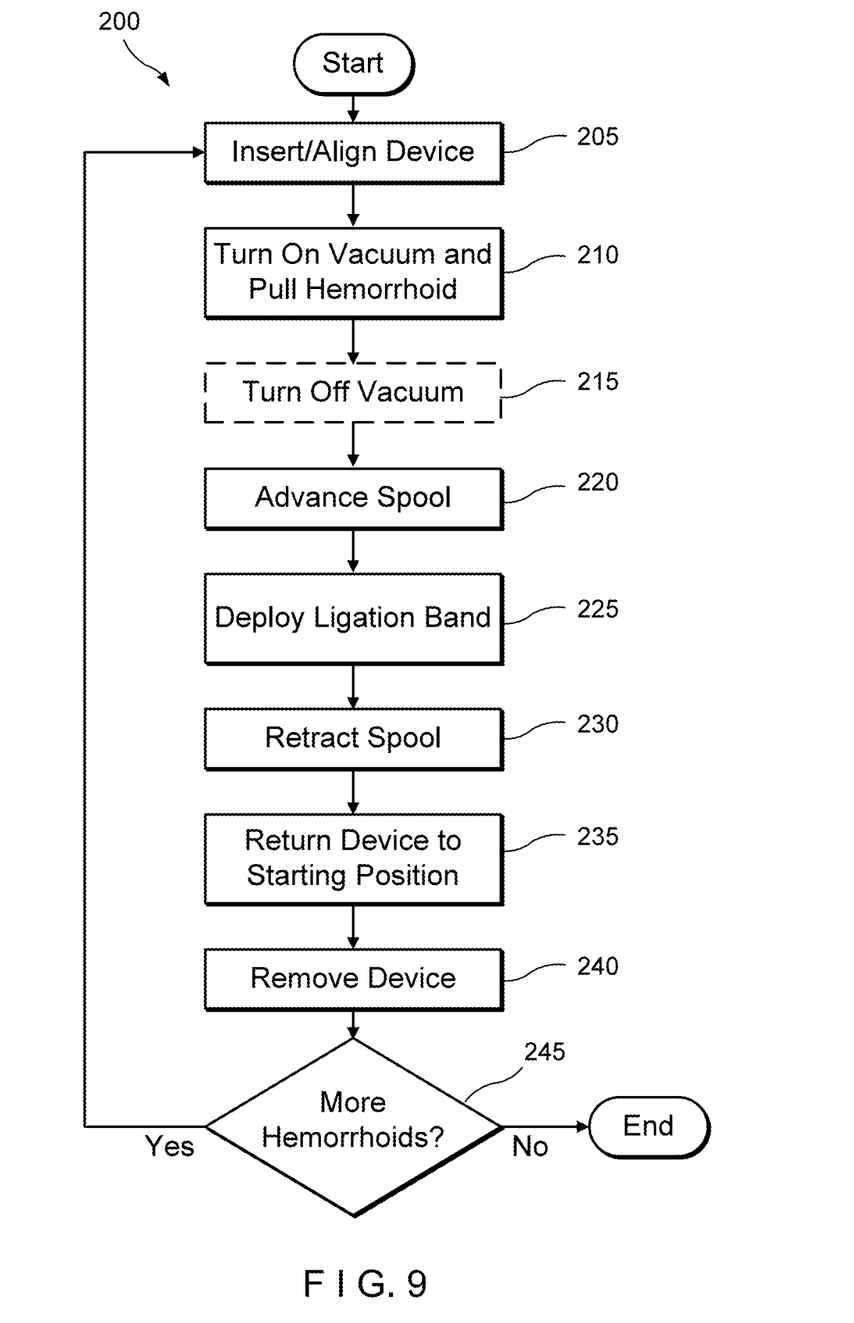
FIG. 9 shows a method for performing the ligation procedure using the device of FIG. 1.

A method 200 will be described for performing the ligation procedure, as shown in FIG. 9. In 205, the device 100, in a first configuration, is inserted into an anus of a patient and aligned with the first hemorrhoid. The camera 116 may be used by a medical professional to visualize a first hemorrhoid on the screen, e.g., so the hemorrhoid is positioned in alignment with the distal end of the distal portion 106 of the device. In 210, when the device is positioned as desired adjacent to the first hemorrhoid, a partial vacuum is imposed on the device 100 using the suction hose and the first hemorrhoid is pulled inside the device 100. A hollow plunger 102 receives the first hemorrhoid in its interior up to the base of the hemorrhoid. In 215, when the hemorrhoid has been drawn into the device as desired, the suction hose may be turned off, if the position of the hemorrhoid is otherwise maintained.

In 220, the device 100 is advanced into a second configuration, closing the flexible pushing portion 122 onto the distal end 106 of the plunger 102. Teeth 126 on each of flexible flanges 124 engage portions of the distal end 106 proximal and adjacent to the ligation bands 150. In 225, the device 100 is advanced to a third configuration, pushing a spool distally the remaining distance and pushing each of the bands distally by one band position so that the first band 150 is deployed around the first hemorrhoid. Steps 220 and 225 may be performed in one continuous drawing motion using the thumb ring 108 and the spool 112.

In 230, the device 100 is advanced into a fourth configuration, retracting the spool 112 and releasing the flexible pushing portion 122 from the confines of the closing sleeve 130. In 235, the device is returned to the first configuration by retracting the spool the remaining distance and returning the deployment sleeve 118 to the proximal position. Steps 230 and 235 may be performed in one continuous pushing motion using the thumb ring 108 and the spool 112.

Figure 10:
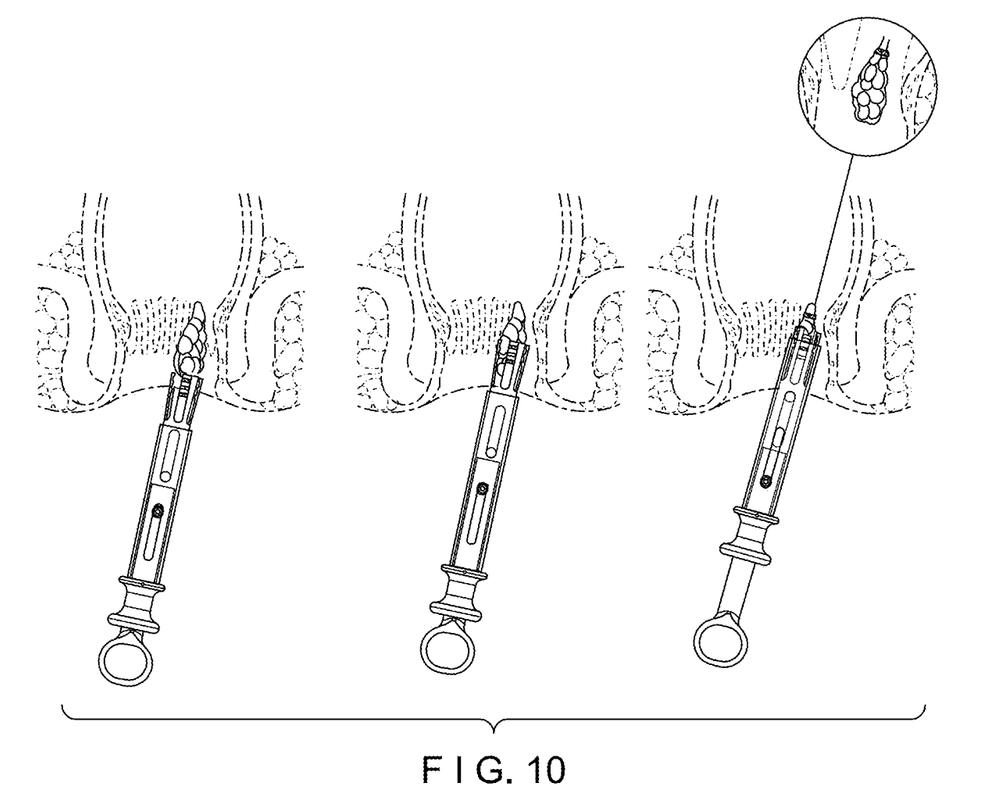
FIG. 10 shows a visualization of an application of a ligation band to a hemorrhoid using the device of FIG. 1.
Figure 11:
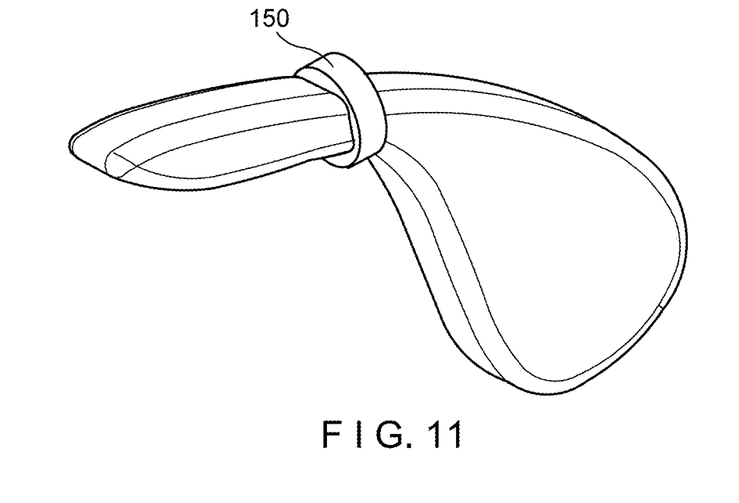
FIG. 11 shows a visualization of the ligation band applied to the base of the hemorrhoid.

In 240, the device 100 is optionally removed from the patient's anus. Alternatively, if it is determined that further hemorrhoids are to be treated, the device 100 may be reoriented in a manner similar to step 205 in a position adjacent to a second hemorrhoid to be treated and the steps 210-240 may be repeated using one of the two remaining ligation bands 150 on the distal end of the plunger 102 which process may then be repeated until all of the targeted hemorrhoids have been treated. When no hemorrhoids remain for ligation the method ends. FIG. 10 shows a visualization of an application of a ligation band to a hemorrhoid using the device of FIG. 1, and FIG. 11 shows a visualization of the ligation band applied to the base of the hemorrhoid.

Thus, it may be seen that the band deployment mechanism 114 utilizes a simple and efficient sliding-based design to perform ligation at low cost. The intuitive drawing mechanism (thumb ring and spool) may reduce or prevent premature deployment by advancing the device at a controlled rate, given a consistent pulling speed from the medical professional. The drawing mechanism is easily manipulatable and reversible if the medical professional decides to reverse the advancement of the spool and, e.g., reapply a vacuum or reorient the device 100. The bands may be colored such that the medical professional may be notified that a band remains loaded on the device 100.

For example, if the second band of a three-band device is colored yellow, deployment of the yellow band (and visualization of said yellow band on the hemorrhoid) will notify the operating medical professional that there is only one band remaining for deployment. In another embodiment, the device 100 has an indexing feature. If the device 100 has three ligation bands loaded thereon at the beginning of the procedure, the indexing feature would reveal the number three. Deployment of a band will reduce the number to two, and so on, until all of the bands are deployed. The indexing feature may use a clicking mechanism that is activated when the device 100 reaches, e.g. the third configuration.

Figure 12:
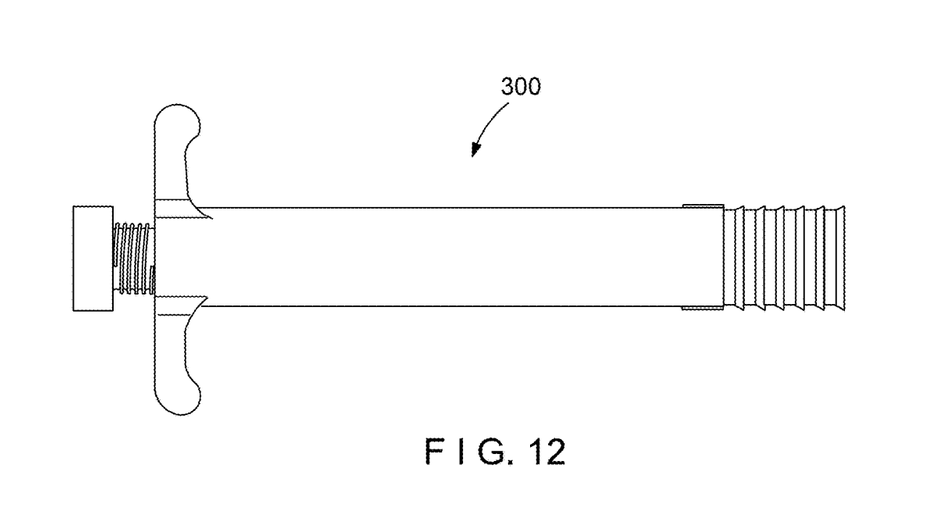
FIG. 12 shows a side view of a second device for ligating hemorrhoids according to a second exemplary embodiment of the present disclosure.
Figure 13:
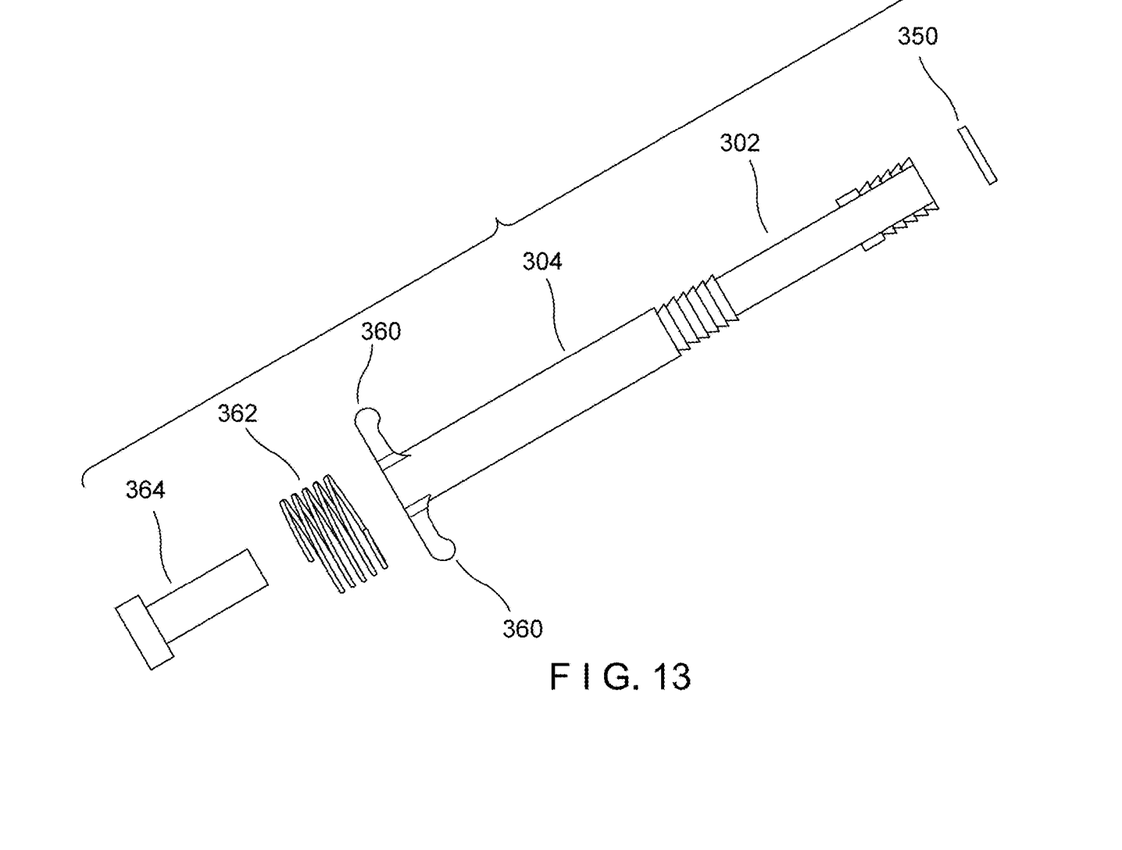
FIG. 13 shows a disassembled view of the device of FIG. 12.
Figure 14:
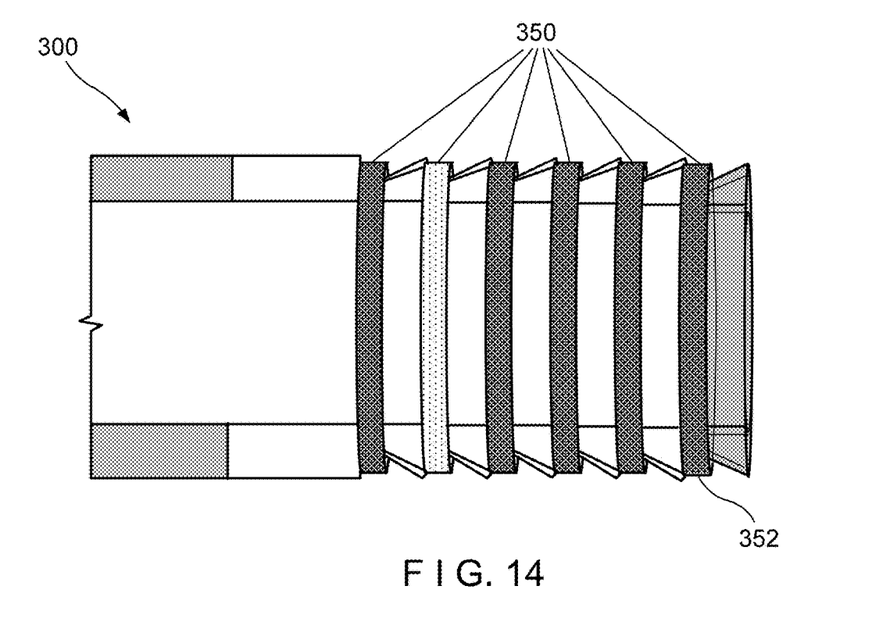
FIG. 14 shows a side view of a distal end of the device of FIG. 12
Figure 15:
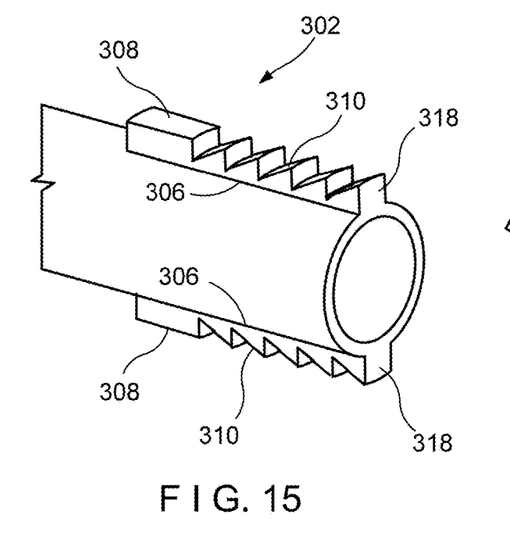
FIG. 15 shows a disassembled perspective view of a plunger of the device of FIG. 12.
Figure 16:
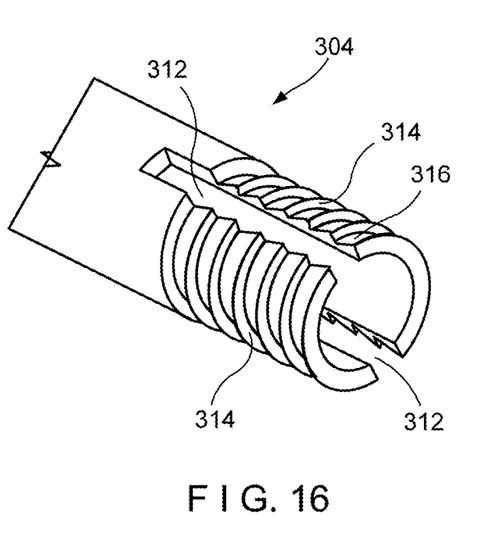
FIG. 16 shows a disassembled perspective view of a rubber band housing of the device of FIG. 12.
Figure 17:
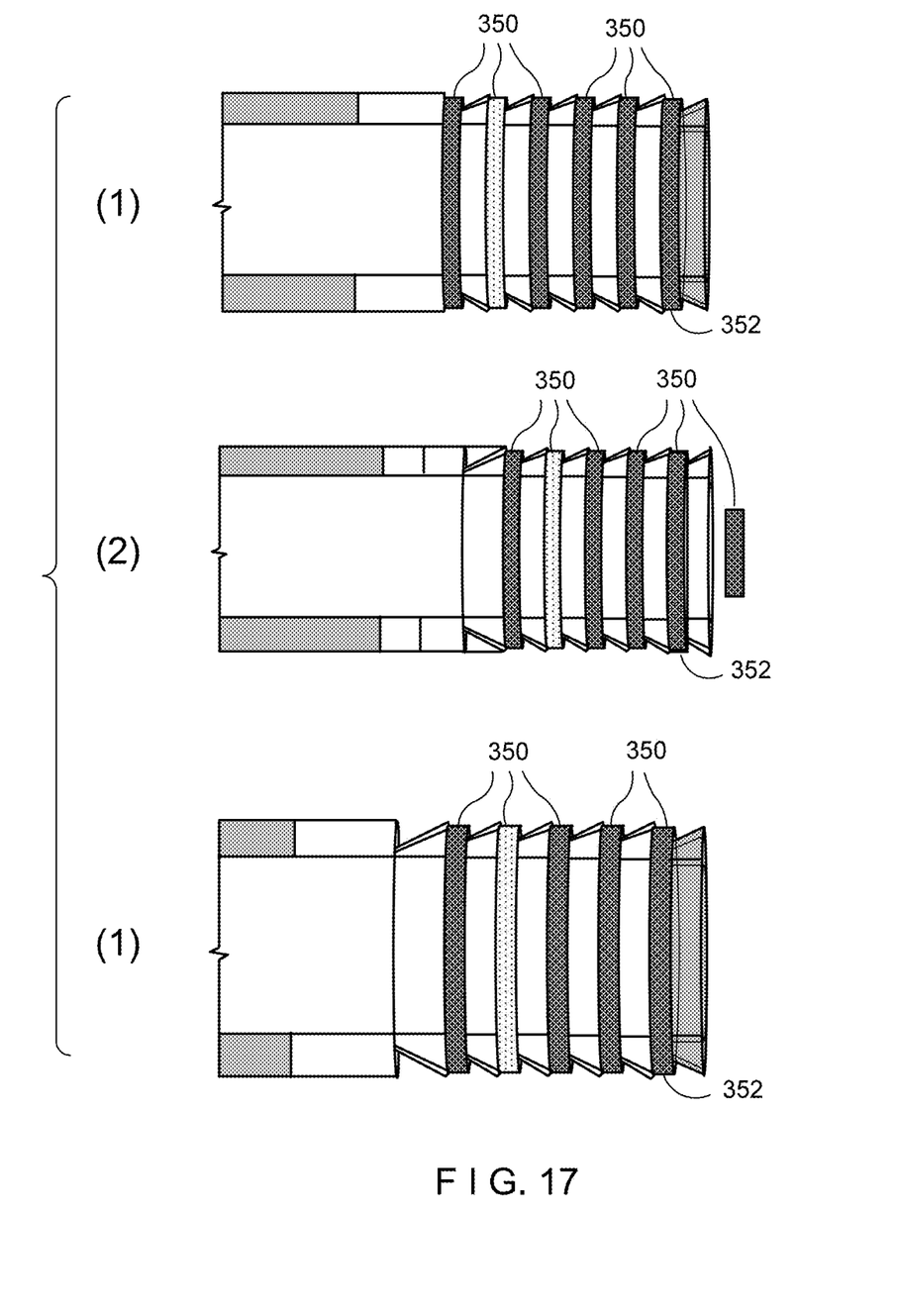
FIG. 17 shows the device of FIG. 12 advancing through a series of configurations during a ligation procedure.

FIG. 12 shows a device 300 for ligating hemorrhoids according to a second exemplary embodiment of the present disclosure. The device 300 may be further understood with respect to FIGS. 13 and 15-16, showing views of the device 300 in a disassembled state, and FIGS. 14 and 17, showing views of the device in an assembled state. The device 300 includes a plunger 302, a rubber band housing 304 and a plurality of ligation bands 350 loaded onto the distal end of the assembled device 300. The housing 304 may be an elongate body, e.g., a hollow tube extending along a longitudinal axis, and the plunger 302 may be an elongate body, disposed along the longitudinal axis and coaxial to the housing 304. The plunger 302 may be disposed at least partially in the housing 304. A proximal end of the rubber band housing 304 has protrusions 360 extending radially outward for supporting, e.g., the index and middle fingers of a user of the device 300 and a push button 364 operable by a medical professional, e.g., a user's thumb.

A distal portion of the push button 364 is coupled to the plunger 302 in the interior of the rubber band housing 304 when the device 300 is in the assembled state, such that operation of the push button 364, i.e., pushing the push button 364 distally, also moves the plunger 302 distally. The proximal (i.e., unactuated) positioning of the plunger 302 may be considered a first configuration of the device 300, while the distal positioning of the plunger 302 may be considered a second configuration of the device 300. A spring 362 is compressible between the push button 364 and the rubber band housing 304 when the push button 364 is depressed and the device advances to the second configuration and releasing the push button 364 allows the push button 364 and the plunger 302 to return to the first configuration.

As shown in FIG. 15, the distal end of the plunger 302 has two tapered pushing portions 306 protruding radially from opposing sides of the plunger 302. Each pushing portion 306 has a proximal portion 308 and a stepped section 310. The proximal portion 308 is keyed to a notch 312 in the rubber band housing 304 such that sliding the portion 308 within the notch 312 aligns the plunger 302 as desired with the rubber band housing 304. Each step of the stepped sections 310 slopes distally and radially outward. In one embodiment the plunger 302 has five steps in each stepped section 310, however, more or less steps may be used. A most distal step 318 is used to push a most distal ligation band 352 off the distal end of the rubber band housing 304, to be explained in detail below.

As shown in FIG. 16, the distal portion of the rubber band housing 304 has a plurality of notches 312 sized and shaped to receive the tapered pushing portions 306 of the plunger 302 and to align the plunger 302 and the rubber band housing 304 during the ligation procedure. Each of the notches 312 extends proximally into the housing 304 such that portion 308 of the plunger 302 is received therein when the plunger 302 and the housing 304 are aligned. The housing 304 has two grooved sections 314 on opposite sides of the notches 312. The two grooved sections 314 slope radially outward and distally in a manner substantially similar to the stepped sections 310 of the plunger. The grooved sections 314 extend about the circumference of the housing 304 with the exception of the space made by the notches 312.

When the plunger 302 and the housing 304 are aligned the stepped sections 310 fill in the gaps formed by the notches 312 and substantially complete a plurality of grooves (e.g., circular) configured for loading the bands 350 therein. However, the most distal groove 316 of the grooved sections 314 extends past the most distal step 318 of the stepped sections 310. In other words, where this embodiment of the plunger 302 comprises five steps in each of the stepped sections 310, this embodiment of the grooved sections 314 has six grooves, wherein five of the grooves align with the five steps and the sixth groove extends past the furthest extent of the plunger 302, as shown in FIG. 14.

The device 300 is advanceable from the first configuration to the second configuration and back to the first configuration, as shown in FIG. 17. In the first configuration the plunger 302 and the housing 304 are aligned as described above and the rubber bands 350 are loaded thereon, including onto the most distal groove 316, as shown in FIG. 14. In other words, the most distal band 352 extends around the most distal groove 316 and across the notches 312, distal to the most distal step 318 of the stepped sections 310. The first configuration may be considered a loading configuration.

To advance the device 300 into the second configuration a medical professional pushes the plunger 302 distally with respect to the housing 304. The stepped sections 310 push the rubber bands 350 distally at the two opposing stepped locations. Thus, it may be seen that each rubber band 350 is pushed forward by one groove of the grooved sections 314, while the most distal step 318 pushes the most distal band 352 off the distal end of the rubber band housing 304.

To reload the device 300, it is brought back into the first configuration. Drawing the plunger 302 proximally allows the second most distal band to assume the original position of the most distal band 352. The taper of the grooves 314 allows each of the remaining rubber bands 350 to slide up and over the steps of the stepped sections 310 while remaining in their respective grooves. Thus, each of the remaining bands 350 has been shifted forward by one space, and the remaining bands 350 may be deployed in a manner substantially similar to that described above for the most distal band 352, until the bands 350 are exhausted.

Figure 18:
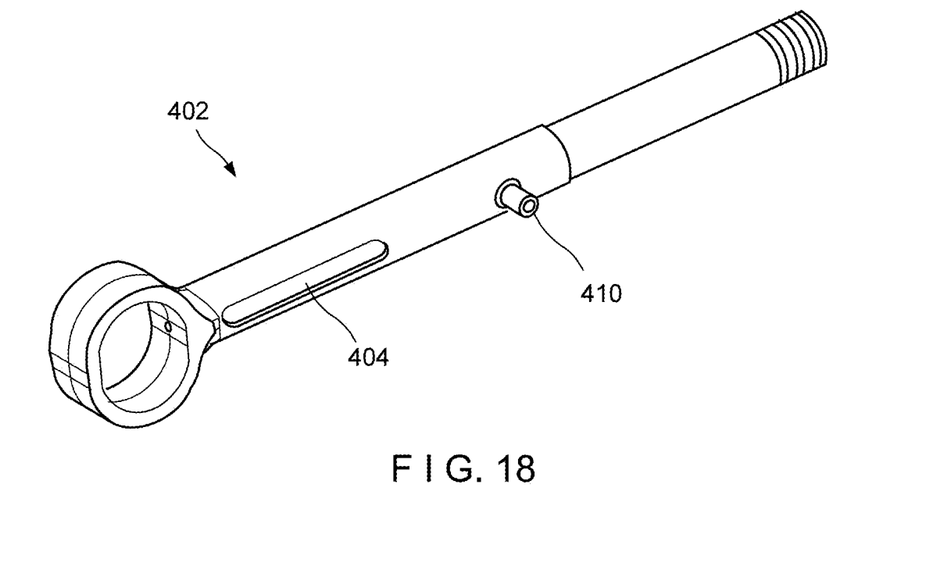
FIG. 18 shows a perspective view of a third device for ligating hemorrhoids according to a third exemplary embodiment of the present disclosure.
Figure 19:
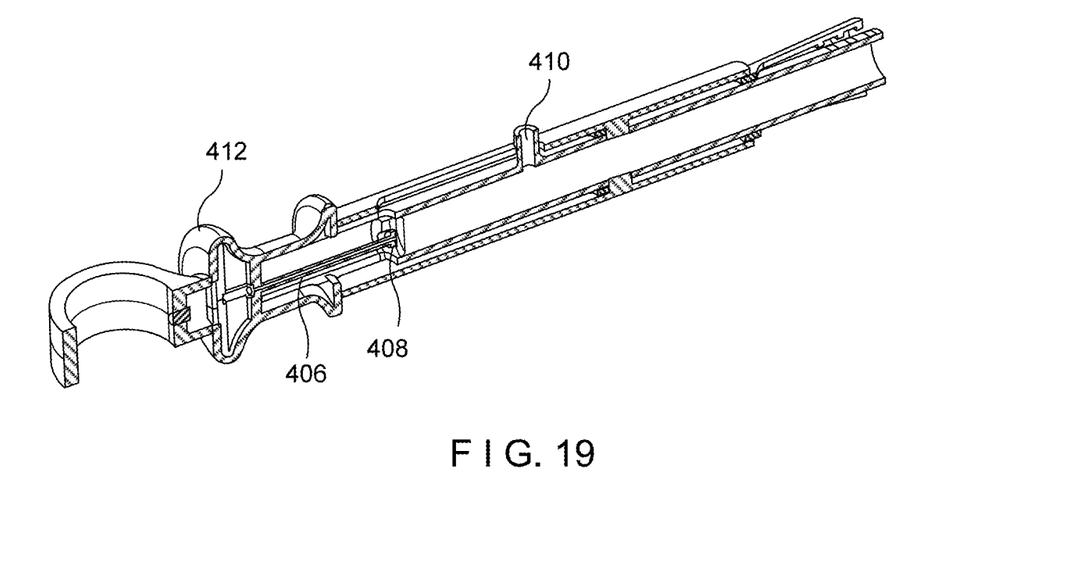
FIG. 19 shows a cutaway perspective view of the device of FIG. 18.
Figure 20:
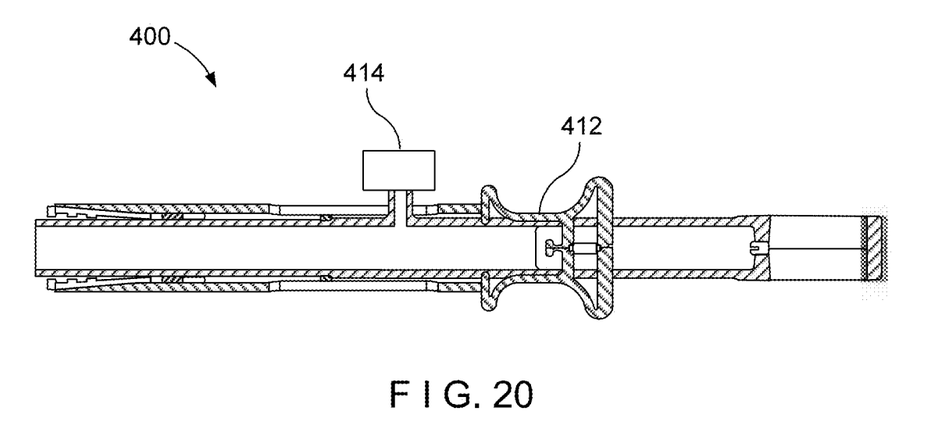
FIG. 20 shows a cutaway side view of the device of FIG. 18.

FIGS. 18-20 show a device 400 for ligating hemorrhoids according to a third exemplary embodiment of the present disclosure. The device 400 has a band deployment mechanism similar to the device 100. However, the device 400 comprises a dual-action plunger mechanism for drawing a vacuum in addition to deploying the ligation bands. In addition to the device components described with respect to the device 100, the device 400 further includes a proximal slot 404 in the plunger 402. The spool 412 has an interior portion extending through the slot 404 and a vacuum shaft 406 extending distally therefrom. The vacuum shaft 406 extends to a vacuum seal 408 in the interior of the plunger 402 that forms an airtight seal therein, such that drawing the spool 412 proximally with respect to the plunger 402 induces suction at the distal end of the plunger 402 and at the vacuum port 410. In the third embodiment, the vacuum port 410 has a removable rubber cap 414.

Figure 21:
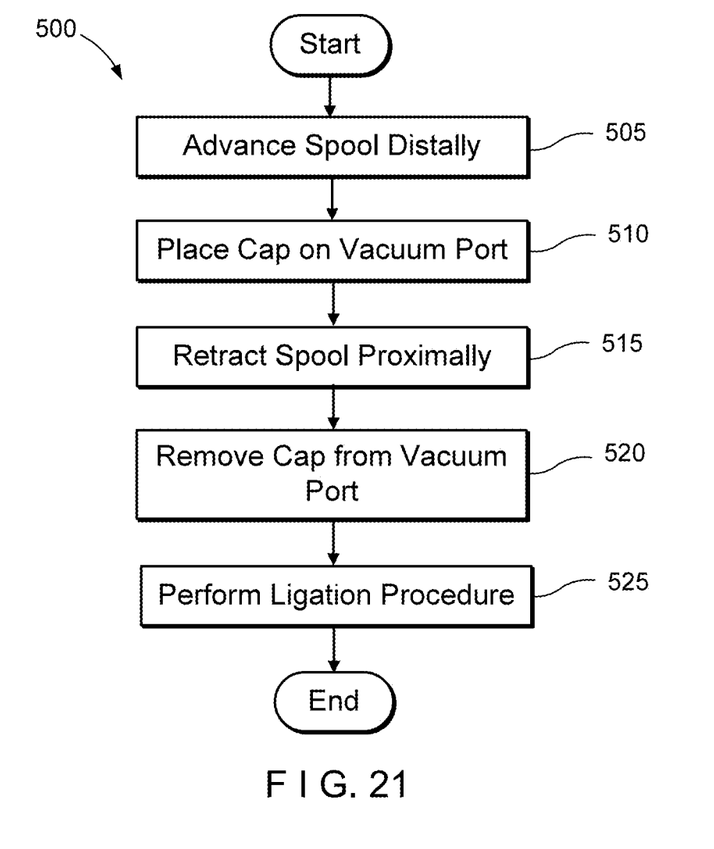
FIG. 21 shows a method for drawing a hemorrhoid into the device of FIG. 18.

The operation of the device 400 may be described with respect to a method 500 for drawing a hemorrhoid with the spool 412, as shown in FIG. 21, prior to implementing the previously described series of configurations for deploying a ligation band. The method 500 begins with the device 400 in an unactuated starting position. The spool 412 is disposed proximally toward the thumb ring 108 and the rubber cap 414 is removed from the vacuum port 410.

In 505, the spool 412 is advanced to a distal position. Air in the hollow interior of the plunger 402 is expelled via the distal end of the plunger 402 and the vacuum port 410. In 510, the rubber cap 414 is placed on the vacuum port 410. In 515, the spool is retracted proximally, thus imposing a vacuum at the distal end of the plunger 402 and receiving hemorrhoidal tissue therein. In 520, the rubber cap 408 is removed from the vacuum port 410 and the device 400 is operable to deploy a ligation band substantially similarly to the operation of device 100.

In this manner, the hemorrhoid is drawn into the distal end of the plunger 402, yet the opening of the vacuum port 410 allows the spool to be advanced/retracted without imposing pressure/vacuum on the distal end because the displaced air can flow through the vacuum port 410. Thus, the spool 412 of the device 400 is a dual-action spool operable to draw the hemorrhoidal tissue and subsequently apply a ligation band to the drawn tissue in 525.

Figure 22:
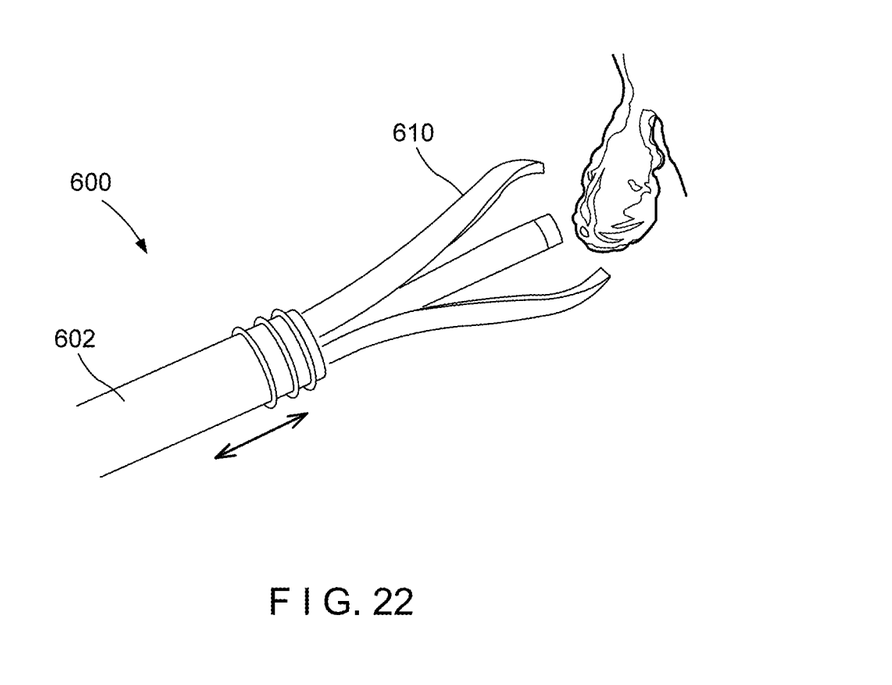
FIG. 22 shows a distal end of a fourth device for ligating hemorrhoids according to a fourth exemplary embodiment of the present disclosure.

FIG. 22 shows a distal end of a device 600 for ligating hemorrhoids according to a fourth exemplary embodiment of the present disclosure. The device 600 has a band deployment mechanism similar to the device 100. However, the device 600 includes jaws 610 for grasping the hemorrhoid and pulling the hemorrhoid into the plunger 602 instead of using suction.

Figure 23:
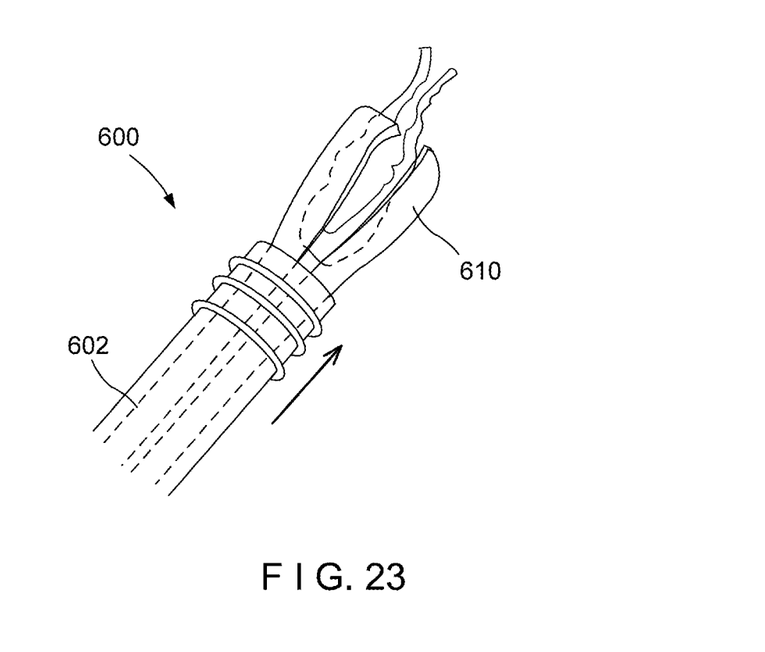
FIG. 23 shows the distal end of the device of FIG. 22 with jaws in a closed position around the hemorrhoid.

The jaws 610 are coupled to a proximal handle portion that may be slid proximally and distally with respect to the plunger 602 and the band deployment mechanism. When the handle portion is in a distal position, the jaws 610 are in an open position, as shown in FIG. 22. When the handle portion is drawn proximally, the jaws 610 are drawn within the plunger 602, as shown in FIG. 23. The proximal motion acts to close the jaws 610 around the hemorrhoid and bring a substantial portion of the hemorrhoid within the plunger 602, such that only the base is exposed distal to the device 600. Once the hemorrhoid is drawn within the plunger 602 the previously described band deployment mechanism may be implemented to apply a ligation band to the base of the hemorrhoid. The proximal handle portion may be pushed distally with respect to the plunger 602 to open the jaws 610 and release the banded hemorrhoid.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiments disclosed, but rather, modifications are also covered within the scope of the present invention as defined by the appended claims.

The invention claimed is:

1. A device, comprising:
at least one ligation band;
an elongated hollow member having an open distal end for receiving tissue therein and at least one exterior groove for loading the at least one ligation band thereon;
a band deployment sleeve slidable over an exterior of the elongated hollow member, the band deployment sleeve having a distal portion configured to move from a radially expanded position in which, when the band deployment sleeve slides longitudinally over the elongated hollow member, the distal portion is disengaged from the at least one ligation band, to a radially contracted position in which, when the band deployment sleeve slides longitudinally over the elongated hollow member, the distal portion engages the at least one ligation band; and
a closing sleeve slidable over an exterior of the band deployment sleeve so that moving the closing sleeve distally over the distal portion of the band deployment sleeve constrains the distal portion from the radially expanded position into the radially contracted position and retracting the closing sleeve proximally over the distal portion of the band deployment sleeve releases the distal portion from the radially contracted position into the radially expanded position.

2. The device of claim 1, further comprising:
a pin on an interior of the closing sleeve slidable within a slot in the band deployment sleeve, wherein moving the closing sleeve distally over the distal portion of the band deployment sleeve causes the pin to slide distally within the slot until the pin abuts a distal end of the slot and further distal movement of the closing sleeve engages the pin with the distal end of the slot and moves the band deployment sleeve distally.

3. The device of claim 2, wherein, when the at least one ligation band is loaded in the at least one exterior groove, the distal movement of the band deployment sleeve pushes the at least one ligation band out of the at least one exterior groove and off the distal end of the elongated hollow member.

4. The device of claim 2, wherein the elongated hollow member has a plurality of exterior grooves arranged in a longitudinal series on the elongated hollow member for loading a plurality of ligation bands thereon,
wherein, when each of the plurality of ligation bands are loaded in the plurality of exterior grooves, the distal movement of the band deployment sleeve in the radially contracted position pushes a furthest distal ligation band out of a furthest distal exterior groove and off the distal end of the elongated hollow member and shifts additional ligation bands distally by one exterior groove of the longitudinal series.

5. The device of claim 4, wherein the distal portion of the band deployment sleeve comprises a plurality of flexible members, each flexible member having a plurality of teeth arranged in a longitudinal series on the flexible member so that the distal movement of the band deployment sleeve in the radially contracted position causes each tooth to engage one of the plurality of ligation bands.

6. The device of claim 5, wherein, after the further distal movement of the closing sleeve, moving the closing sleeve proximally over the distal portion of the band deployment sleeve causes the pin to slide proximally within the slot until the pin abuts a proximal end of the slot and further proximal movement of the closing sleeve engages the pin with the proximal end of the slot and moves the band deployment sleeve proximally.

7. The device of claim 6, wherein the proximal movement of the closing sleeve causes the band deployment sleeve to open into the radially expanded position and the further proximal movement of the closing sleeve returns the band deployment sleeve to an initial position without causing the teeth to engage the additional ligation bands.

8. The device of claim 4, wherein at least one of the plurality of ligation bands is color-coded for notifying an operating medical professional of an additional number of ligation bands.

9. The device of claim 1, further comprising:
a vacuum port extending transverse to the elongated hollow member for attaching a suction hose and inducing suction at the open distal end of the elongated hollow member.

10. The device of claim 1, further comprising:
a spool coupled to a proximal end of the closing sleeve and slidable over the elongated hollow member; and
a thumb ring coupled to a proximal end of the elongated hollow member,
wherein separating the thumb ring and the spool causes the closing sleeve to move distally.

* * * * *